United States Patent
Chassot et al.

(10) Patent No.: US 7,070,626 B2
(45) Date of Patent: Jul. 4, 2006

(54) (P-AMINO-HYDROXYPHENYL)-ACRYLAMIDE DERIVATIVES AND DYES CONTAINING SAID COMPOUNDS

(75) Inventors: Laurent Chassot, Praroman (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 427 days.

(21) Appl. No.: 10/275,326

(22) PCT Filed: Oct. 19, 2001

(86) PCT No.: PCT/EP01/12126

§ 371 (c)(1),
(2), (4) Date: Nov. 7, 2002

(87) PCT Pub. No.: WO02/079144

PCT Pub. Date: Oct. 10, 2002

(65) Prior Publication Data

US 2003/0192132 A1  Oct. 16, 2003

(30) Foreign Application Priority Data

Mar. 30, 2001  (DE) .................................. 101 15 994

(51) Int. Cl.
*A61K 7/13* (2006.01)

(52) U.S. Cl. ....................... 8/405; 8/406; 8/410; 8/421; 8/423; 564/305

(58) Field of Classification Search ............ 8/405, 8/406, 410, 421, 423; 564/305
See application file for complete search history.

(56) References Cited

U.S. PATENT DOCUMENTS 5,643,925 A  * 7/1997 Naruto et al. ............... 514/311
5,780,483 A  * 7/1998 Widdowson et al. ....... 514/311

FOREIGN PATENT DOCUMENTS

DE       196 07 751 A      9/1997

OTHER PUBLICATIONS

Jaynes et al. Bioorganic & Medicinal Chemistry Letters (1993), 3(8), 1531–6.*
Organic Synthesis, Chapter 3, "Protection for Phenols", pp. 142–175, Wiley Intersciences, 1991.

* cited by examiner

*Primary Examiner*—Margaret Einsmann
*Assistant Examiner*—Eisa Elhilo
(74) *Attorney, Agent, or Firm*—Michael J. Striker

(57) ABSTRACT

The object of the invention are (p-aminohydroxyphenyl) acrylamide derivatives of general formula (I) or the physiologically tolerated, water-soluble salts thereof

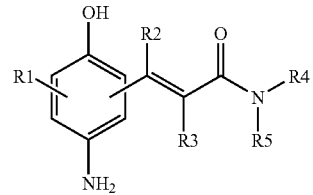

and oxidative coloring agents for keratin fibers, containing these compounds.

9 Claims, No Drawings

(P-AMINO-HYDROXYPHENYL)-ACRYLAMIDE DERIVATIVES AND DYES CONTAINING SAID COMPOUNDS

BACKGROUND OF THE INVENTION

1. Field of the Invention

The invention relates to new (p-aminohydroxyphenyl) acrylamide derivatives and dyeing agents containing these compounds for dyeing keratin fibers, particularly human hair.

2. Description of the Related Art

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol, 1,4-diaminobenzene and 4,5-diaminopyrazole-1-(2'-hydroxyethyl)-pyrazole, and suitable couplers are, for example, resorcinol, 2-methylresorcinol, 1-naphthol, 3-aminophenol, m-phenylenediamine, 2-amino-4-(2'-hydroxyethyl)aminoanisole, 1,3-diamino-4-(2'-hydroxyethoxy)benzene and 2,4-diamino-5-fluorotoluene.

The oxidation dyes used for dyeing human hair must meet numerous requirements in addition to that of being able to produce colorations of the desired intensity. For example, these dyes must be harmless from a toxicological and dermatological standpoint, and the hair colorations obtained must have good light fastness, resistance to permanent waving, acid fastness and rubbing fastness. In any case, however, in the absence of exposure to light, rubbing and chemicals, such colorations must remain stable over a period of at least 4 to 6 weeks. Moreover, by combining appropriate developers and couplers, it must be possible to create a wide range of different color shades.

To attain natural and, in particular, fashionable color shades in the red region, p-aminophenol, alone or in admixture with other developers, in combination with suitable couplers, is primarily used. Attempts have already been made to improve the properties of p-aminophenols by the introduction of substituents. In this regards, the reader is referred to German Unexamined Patent Application DE 196 07 751 which describes colorants containing as developers special substituted p-aminophenol derivatives, for example 5-amino-2-hydroxycinnamic acid.

With the currently known colorants, it is not possible, however, to meet the requirements placed on colorants in all respects. Hence, the need continued to exist for new developers capable of meeting the aforesaid requirements to a particularly high degree.

SUMMARY OF THE INVENTION

Surprisingly, in this respect we have now found that new (p-aminohydroxyphenyl)acrylamide derivatives of general formula (I) meet said requirements placed on developers to a particularly high degree. In fact, when these developers are used with most known couplers, they give intense color shades that are unusually light-fast and wash-fast.

The object of the present invention therefore are (p-aminohydroxyphenyl)acrylamide derivatives of general formula (I) or physiologically tolerated, water-soluble salts thereof

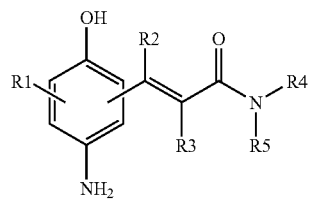

(I)

wherein

R1 denotes hydrogen, a halogen atom (F, Cl, Br, I), a $C_1$–$C_4$-alkyl group, a $C_1$–$C_4$-hydroxyalkyl group or a $C_1$–$C_4$-alkoxy group;

R2 and R3 independently of each other denote hydrogen or a $C_1$–$C_6$-alkyl group;

R4 and R5 independently of each other denote hydrogen, a $C_1$–$C_2$-alkoxy group, a $C_1$–$C_6$-alkyl group, an unsaturated $C_3$–$C_6$-alkyl group, a $C_2$–$C_4$-hydroxyalkyl group, a $C_3$–$C_4$-dihydroxyalkyl group, a $C_2$–$C_4$-aminoalkyl group, a $C_2$–$C_4$-dimethylaminoalkyl group, a $C_2$–$C_4$-acetylaminoalkyl group, a $C_2$–$C_4$-methoxyalkyl group, $C_2$–$C_4$-ethoxyalkyl group, a $C_1$–$C_4$-cyanoalkyl group, a $C_1$–$C_4$-carboxyalkyl group, a $C_1$–$C_4$-aminocarbonylalkyl group, a pyridylmethyl group, a furfuryl group, a thienylmethyl group, a hydrogenated furfuryl group a substituted pyridyl group, a group of formula (II)

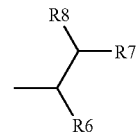

(II)

a group of formula (III)

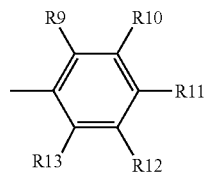

(III)

or a group of formula (IV)

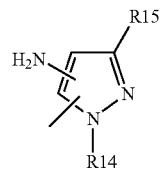

(IV)

or R4 and R5 together with the nitrogen atom form a ring of the following formula

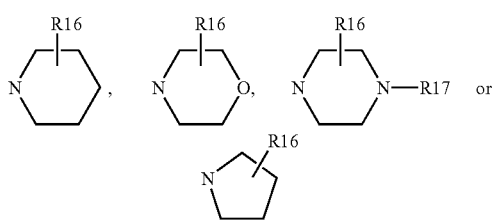

R6 denotes hydrogen, a carboxy group or an aminocarbonyl group;

R7 and R8 independently of each other denote hydrogen, a hydroxyl group, an aminocarbonyl group, a methylthiomethyl group, a phenyl-substituted or hydroxyl-substituted phenyl group or a group of formula

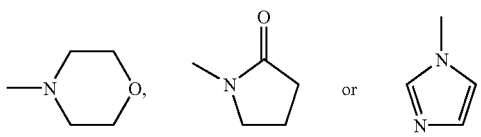

R9, R10, R11, R12 and R13 independently of each other denote hydrogen, a halogen atom (F, Cl, Br, I), a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group, an alkylamino group, a $C_1$–$C_4$-hydroxyalkylamino group, a dialkylamino group, a di($C_1$–$C_4$-hydroxyalkyl)amino group, a ($C_3$–$C_4$-dihydroxyalkyl)amino group, a ($C_1$–$C_4$-hydroxyalkyl)-$C_1$–$C_4$-alkylamino group, a trifluoromethyl group, a —C(O)H group, a —C(O)CH$_3$— group, a —C(O)CF$_3$ group, an —Si(CH$_3$)$_3$ group, a $C_1$–$C_4$-hydroxyalkyl group or a $C_3$–$C_4$ dihydroxyalkyl group, or two adjacent R9 to R13 groups form an —O—CH$_2$—O— bridge;

R14 denotes a $C_1$–$C_4$-alkyl group, a benzyl group or a $C_2$–$C_4$-hydroxyalkyl group;

R15 denotes hydrogen or a $C_1$–$C_6$-alkyl group;

R16 denotes hydrogen, a hydroxyl group, a carboxy group, an aminocarbonyl group or a hydroxymethyl group; and R17 denotes hydrogen or a $C_1$–$C_6$-alkyl group.

Suitable compounds of formula (I) are, for example, the following: 3-(5-amino-2-hydroxyphenyl)-N-cyclopropylacrylamide, 3-(5-amino-2-hydroxyphenyl)-N-propylacrylamide, 3-(5-amino-2-hydroxyphenyl)-1-pyrrolidin-1-ylpropenone, 3-(5-amino-2-hydroxyphenyl)-N-(2-methoxyethyl)acrylamide, 3-(5-amino-2-hydroxyphenyl)-1-morpholin-4-ylpropenone, 3-(5-amino-2-hydroxyphenyl)-N-(1-hydroxymethylpropyl)acrylamide, 3-(5-amino-2-hydroxyphenyl)-N-furan-2-ylmethylacrylamide, 3-(5-amino-2-hydroxyphenyl)-N-methoxy-N-methylacrylamide, 3-(5-amino-2-hydroxyphenyl)-1-(4-methylpiperazin-1-yl)propenone, 3-(5-amino-2-hydroxyphenyl)-1-(4-hydroxypiperidin-1-yl)-propenone, N-(2-acetylaminoethyl)-3-(5-amino-2-hydroxyphenyl)acrylamide, 3-(5-amino-2-hydroxyphenyl)-N-(2-morpholin-4-ylethyl)acrylamide, 3-(5-amino-2-hydroxyphenyl)-N-[3-(2-ketopyrrolidin-1-yl)propyl]acrylamide, N-allyl-3-(5-amino-2-hydroxyphenyl)acrylamide, 3-(5-amino-2-hydroxyphenyl)-N-(2-hydroxy-1-methylethyl)acryl-amide, 3-(5-amino-2-hydroxyphenyl)-N-[2-(5-nitropyridin-2-yl-amino)ethyl]acrylamide, N-(2-aminoethyl)-3-(5-amino-2-hydroxyphenyl)acrylamide, 3-(5-amino-2-hydroxyphenyl)-N-(3-imidazol-1-ylpropyl) acrylamide, 3-(5-amino-2-hydroxyphenyl)-N-(tetrahydrofuran-2-ylmethyl)acrylamide, 3-(5-amino-2-hydroxyphenyl)-N-(4-aminophenyl)acrylamide, N-[4-amino-2(3)-(2-hydroxyethyl)phenyl]-3-(5-amino-2-hydroxyphenyl)acrylamide, 3-(5-amino-2-hydroxyphenyl)-N-{4-[bis-(2-hydroxyethyl)amino]phenyl}acrylamide, 3-(5-amino-2-hydroxyphenyl)-N-(3-aminophenyl)acrylamide, N-[5-amino-2(4)-(2-hydroxyethoxy)phenyl]-3-(5-amino-2-hydroxyphenyl)acrylamide, 3-(5-amino-2-hydroxyphenyl)-N-[2-chloro-4-(2-hydroxyethylamino)-5-nitrophenyl]acrylamide, N-[4-amino-2-(2-hydroxyethyl)-2H-pyrazol-3-yl]-3-(5-amino-2-hydroxyphenyl)acrylamide, 3-(5-amino-2-hydroxyphenyl)-N-benzo[1,3]dioxol-5-ylacrylamide, 3-(5-amino-2-hydroxyphenyl)-N-(2-hydroxyethyl)-N-methylacrylamide, 3-(5-amino-2-hydroxyphenyl)-N-ethyl-N-(2-hydroxyethyl)acrylamide, 3-(5-amino-2-hydroxyphenyl)-1-(2-hydroxymethylpyrrolidin-1-yl)propenone, 1-[3-(5-amino-2-hydroxyphenyl)acryloyl]pyrrolidin-2-carboxamide, 3-(5-amino-2-hydroxyphenyl)-1-(3-hydroxypiperidin-1-yl)propenone, 3-(5-amino-2-hydroxyphenyl)-N-(2-hydroxy-1-hydroxymethylethyl)acrylamide, 3-(5-amino-2-hydroxyphenyl)-N-ethylacrylamide, 2-[3-(5-amino-2-hydroxyphenyl)acryloylamino]-3-methylbutyric acid, 3-(5-amino-2-hydroxyphenyl)-N-(4-hydroxyphenyl)acrylamide, 3-(5-amino-2-hydroxyphenyl)-N-(1-carbamoyl-2-hydroxyethyl)acrylamide, 3-(5-amino-2-hydroxyphenyl)-N-(4-amino-2(3)-methylphenyl)acrylamide, 3-(5-amino-2-hydroxyphenyl)-N-(3-hydroxy-4-methylphenyl)acrylamide, 3-(5-amino-2-hydroxyphenyl)-N-(2-hydroxy-5-nitrophenyl)acrylamide, 3-(5-amino-2-hydroxyphenyl) acrylic acid, 3-(2-amino-5-hydroxyphenyl)-N-cyclopropylacrylamide, 3-(2-amino-5-hydroxyphenyl)-N-propylacrylamide, 3-(2-amino-5-hydroxyphenyl)-1-pyrrolidin-1-ylpropenone, 3-(2-amino-5-hydroxyphenyl)-N-(2-methoxyethyl)acrylamide, 3-(2-amino-5-hydroxyphenyl)-1-morpholin-4-ylpropenone, 3-(2-amino-5-hydroxyphenyl)-N-(1-hydroxymethylpropyl)acrylamide, 3-(2-amino-5-hydroxyphenyl)-N-furan-2-ylmethylacrylamide, 3-(2-amino-5-hydroxyphenyl)-N-methoxy-N-methylacrylamide, 3-(2-amino-5-hydroxyphenyl)-1-(4-methylpiperazin-1-yl)-propenone, 3-(2-amino-5-hydroxyphenyl)-1-(4-hydroxypiperidin-1-yl) propenone, N-(2-acetylaminoethyl)-3-(2-amino-5-hydroxyphenyl)acrylamide, 3-(2-amino-5-hydroxyphenyl)-N-(2-morpholin-4-ylethyl)acrylamide, 3-(2-amino-5-hydroxyphenyl)-N-[3-(2-ketopyrrolidin-1-yl)propyl]acrylamide, N-allyl-3-(2-amino-5-hydroxyphenyl)acrylamide, 3-(2-amino-5-hydroxyphenyl)-N-(2-hydroxy-1-methylethyl)acrylamide, 3-(2-amino-5-hydroxyphenyl)-N-[2-(5-nitropyridin-2-ylamino)ethyl]acrylamide, N-(2-aminoethyl)-3-(2-amino-5-hydroxyphenyl)acrylamide, 3-(2-amino-5-hydroxyphenyl)-N-(3-imidazol-1-ylpropl) acrylamide, 3-(2-amino-5-hydroxyphenyl)-N-(tetrahydrofuran-2-ylmethyl)acrylamide, 3-(2-amino-5-hydroxyphenyl)-N-aminophenyl)acrylamide, N-[4-amino-2(3)-(2-hydroxyethyl)phenyl]-3-(2-amino-5-hydroxyphenyl)acrylamide, 3-(2-amino-5-hydroxyphenyl)-N-{4-[bis-(2-hydroxyethyl)amino]phenyl}acrylamide, 3-(2-amino-5-hydroxyphenyl)-N-(3-aminophenyl)acrylamide, N-[5-amino-2-(4)-(2-hydroxyethoxy)phenyl]-3-(2-amino-5-hydroxyphenyl)acrylamide, 3-(2-amino-5-hydroxyphenyl)-

N-[2-chloro-4-(2-hydroxyethylamino)-5-nitrophenyl]-acrylamide, N-[4-amino-2-(2-hydroxyethyl)-2H-pyrazol-3-yl]-3-(2-amino-5-hydroxyphenyl)acrylamide, 3-(2-amino-5-hydroxyphenyl)-N-benzo[1,3]dioxol-5-ylacrylamide, 3-(2-amino-5-hydroxyphenyl)-N-(2-hydroxyethyl)-N-methylacrylamide, 3-(2-amino-5-hydroxyphenyl)-N-ethyl-N-(2-hydroxyethyl)acrylamide, 3-(2-amino-5-hydroxyphenyl)-1-(2-hydroxymethylpyrrolidin-1-yl)propenone, 1-[3-(2-amino-5-hydroxyphenyl)acryloyl]pyrrolidin-2-carboxamide, 3-(2-amino-5-hydroxyphenyl)-1-(3-hydroxypiperidin-1-yl)propenone, 3-(2-amino-5-hydroxyphenyl)-N-(2-hydroxy-1-hydroxymethylethyl)acrylamide, 3-(2-amino-5-hydroxyphenyl)-N-ethylacrylamide, 2-[3-(2-amino-5-hydroxyphenyl)acryloylamino]-3-methylbutyric acid, 3-(2-amino-5-hydroxyphenyl)-N-(4-hydroxyphenyl)acrylamide, 3-(2-amino-5-hydroxyphenyl)-N-(1-carbamoyl-2-hydroxyethyl)acrylamide, 3-(2-amino-5-hydroxyphenyl)-N-(4-amino-2(3)-methylphenyl)acrylamide, 3-(2-amino-5-hydroxyphenyl)-N-(3-hydroxy-4-methylphenyl)acrylamide, 3-(2-amino-5-hydroxyphenyl)-N-(2-hydroxy-5-nitrophenyl)acrylamide and 3-(2-amino-5-hydroxyphenyl)acrylic acid and the physiologically tolerated salts thereof.

Preferred compounds of formula (I) are those wherein (i) one, several or all R1, R2 and R3 groups denote hydrogen and/or (ii) R4 denotes a $C_1$–$C_2$-alkyl group, a methoxy group or a $C_2$–$C_4$-hydroxyalkyl group and R5 denotes a $C_2$–$C_4$-hydroxyalkyl group and/or (iii) R4 and R5 independently of each other denote hydrogen, a $C_1$–$C_4$-alkyl group, an unsaturated $C_1$–$C_6$-alkyl group, a $C_2$–$C_4$-hydroxyalkyl group, a $C_3$–$C_4$-dihydroxyalkyl group, a furfuryl group a substituted phenyl group of formula (III) or a substituted pyrazolyl group of formula (IV) and/or (iv) R4 denotes hydrogen and R5 denotes a $C_1$–$C_4$-alkyl group, an unsaturated $C_3$–$C_6$-alkyl group, a $C_2$–$C_4$-hydroxyalkyl group, a $C_3$–$C_4$-dihydroxyalkyl group, a furfuryl group, a substituted phenyl group of formula (III) or a substituted pyrazolyl group of formula (IV).

Particularly preferred are the following compounds of formula (I): 3-(5-amino-2-hydroxyphenyl)-N-ethylacrylamide, 3-(2-amino-5-hydroxyphenyl)-N-ethylacrylamide, 3-(5-amino-2-hydroxyphenyl)-N-(4-hydroxyphenyl)acrylamide, 3-(2-amino-5-hydroxyphenyl)-N-(4-hydroxyphenyl)acrylamide, 3-(5-amino-2-hydroxyphenyl)-N-(4-aminophenyl)acrylamide, 3-(2-amino-5-hydroxyphenyl)-N-(4-aminophenyl)acrylamide, N-[4-amino-2-(2-hydroxyethyl)-2H-pyrazol-3-yl]-3-(5-amino-2-hydroxyphenyl)acrylamide and N-[4-amino-2-(2-hydroxyethyl)-2H-pyrazol-3-yl]-3-(2-amino-5-hydroxyphenyl)acrylamide and the physiologically tolerated salts thereof.

The compounds of formula (I) can be used as the free bases as well as in the form of their physiologically tolerated salts with inorganic or organic acids, for example hydrochloric acid, sulfuric acid, phosphoric acid, acetic acid, propionic acid, lactic acid or citric acid.

The aminophenol derivatives of formula (I) of the invention can be prepared by methods of synthesis known from the literature. For example, the synthesis of the compounds of the invention can be carried out as follows:

by aminolysis of a substituted benzene of formula (V)

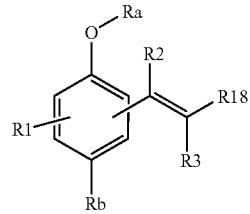

(V)

with an amine of formula NHR4R5 followed by elimination of the protective group and/or reduction of the nitro group, wherein Ra stands for an appropriate protective group as described, for example, in Organic Synthesis, Chapter 3, "Protection for Phenols", p, 143 ff, Wiley Interscience, 1991; Rb stands for NHRa or $NO_2$, R18 denotes a carboxylic acid group, a carboxylic acid chloride group, a carboxylate ester group or a carboxylic anhydride group, and the R1, R2, R3, R4 and R5 group have the same meaning as in formula (I).

The compounds of formula (I) of the invention can be used, in particular, as developers in oxidative colorants for keratin fibers. They make it possible to produce a wide range of different color shades going from blond to brown to purple and all the way to violet shades.

Another object of the invention are therefore agents for oxidative dyeing of keratin fibers, for example hair, furs, feathers or wool, particularly human hair, based on a developer-coupler combination, which as developer contain at least one (p-aminohydroxyphenyl)acrylamide derivative of formula (I).

The colorant of the invention contains the aminophenol derivative of formula (I) in an amount from about 0.005 to 20 weight percent, an amount of about 0.01 to 5.0 weight percent and particularly 0.1 to 2.5 weight percent being preferred.

Preferred couplers are N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 1,3-diamino-4-(3-hydroxypropoxy)benzene, 1,3-diamino-4-(2-methoxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2- methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4[2H]benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

Although the advantageous properties of the aminophenol derivatives of formula (I) described herein suggest that they alone be used as developers, it is, of course, also possible to use the p-aminophenol derivatives of formula (I) together with other known developers, for example with 1,4-diaminobenzene, 2,5-diaminotoluene, 2-(2,5-diaminophenyl)ethyl alcohol, 1-(2,5-diaminophenyl)ethyl alcohol, N,N-bis-(2'-hydroxyethyl)-1,4-diaminobenzene, 4-aminophenol and the derivatives thereof, for example 4-amino-3-methylphenol, pyrazole derivatives, for example 4,5-diamino-1-(2-hydroxyethyl)pyrazole, 4,5-diamino-1-benzylpyrazole and 4,5-diamino-1-(4-methylbenzyl)pyrazole, or tetraaminopyrimidines.

The couplers and developers can be present in the colorant of the invention either individually or in admixture with one another, the total amount of each of the couplers and developers in the colorant of the invention being about 0.005 to 20 wt. % preferably about 0.01 to 5 wt. % and particularly 0.1 to 2.5 wt. % (based on the total amount of colorant).

The total amount of the developer-coupler combination contained in the colorant described herein is preferably about 0.01 to 20 wt. %, an amount of about 0.02 to 10 wt. % and especially 0.2 to 6.0 wt. % being particularly preferred. In general, the developers and couplers are used in approximately equimolar amounts. In this respect, it is not disadvantageous, however, if the developers are present in a certain excess or deficiency.

Moreover, the colorant of the invention can also contain other dye components, for example 6-amino-2-methylphenol and 2-amino-5-methylphenol, as well as common direct dyes, for example triphenylmethane dyes such as 4-[(4'-aminophenyl)-(4'-imino-2",5"-cyclohexadien-1"-ylidene)methyl]-2-methylaminobenzene monohydrochloride (Color Index [C.I.] 42 510) and 4-[(4'-amino-3'-methylphenyl)-(4"-imino-3"-methyl-2",5"-cyclohexadien-1"-ylidene)methyl]-2-methylaminobenzene monohydrochloride (C.I. 42 520), aromatic nitro dyes such as 4-(2'-hydroxyethyl)aminonitrotoluene, 2-amino-4,6-dinitrophenol, 2-amino-5-(2'-hydroxyethyl) aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-(2'-ureidoethyl)amino-4-nitrobenzene, azo dyes such as sodium 6-[(4'-aminophenyl)azo]-5-hydroxynaphthalene-1-sulfonate (C.I. 14 805) and disperse dyes, for example 1,4-diaminoanthraquinone and 1,4,5,8-tetraaminoanthraquinone. The colorants of the invention can contain the aforesaid dye components in an amount from about 0.1 to 4 wt. %.

The couplers and developers as well as the other dye components, provided they are bases, can, of course, also be used in the form of their physiologically tolerated salts with organic or inorganic acids, for example hydrochloric acid or sulfuric acid, or—if they contain aromatic OH groups—in the form of their salts with bases, for example as alkali metal phenoxides.

Moreover, if the colorants are to be used for coloring hair, they can also contain other common cosmetic additives, for example antioxidants such as ascorbic acid, thioglycolic acid or sodium sulfite, as well as perfume oils, complexing agents, wetting agents, emulsifiers, thickeners and hair-care agents.

The colorant of the invention can be in the form of, for example, a solution, particularly an aqueous or aqueous-alcoholic solution. A particularly preferred formulation form, however, is a cream, gel or emulsion. Such a composition consists of a mixture of the dye components and the usual additives employed for such compositions.

Common additives to solutions, creams, emulsions or gels are, for example solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The said constituents are used in amounts commonly employed for such purposes, for example the wetting agents and emulsifiers at a concentration of about 0.5 to 30 wt. %, the thickeners in an amount from about 0.1 to 30 wt. % and the hair-care agents at a concentration from about 0.1 to 5 wt. %.

Depending on the composition, the colorant of the invention can be weakly acidic, neutral or alkaline. In particular, it can have a pH of about 6.5 to 11.5. The adjustment to a basic pH is preferably made with ammonia, but it can also be made with an organic amine, for example with monoethanolamine and triethanolamine, or with an inorganic base such as sodium hydroxide and potassium hydroxide. The adjustment to an acidic pH can be made with an inorganic or organic acid, for example phosphoric, acetic, citric or tartaric acid.

For oxidative dyeing of hair, the afore-described colorant is mixed with an oxidant just before use, and an amount sufficient for hair treatment, generally about 60 to 200 grams, of this mixture, depending on the hair fullness, is applied to the hair.

Suitable oxidants for developing the hair coloration are primarily hydrogen peroxide or its products of addition to urea, melamine, sodium borate or sodium carbonate in the form of a 3 to 12% and preferably 6% aqueous solution, atmospheric oxygen also being suitable. When a 6% hydrogen peroxide solution is used as oxidant, the weight ratio of hair colorant to oxidant is from 5:1 to 1:2 and preferably 1:1. Higher amounts of oxidant are used especially with higher dye concentrations in the hair colorant or when stronger bleaching of the hair is wanted at the same time. The mixture is allowed to act on the hair at 15 to 50° C. for about 10 to 45 minutes, preferably 30 minutes. The hair is then rinsed with water and dried. Optionally, following this rinsing, the hair is washed with a shampoo and optionally post-rinsed with a weak organic acid such as citric acid or tartaric acid. The hair is then dried.

The colorants of the invention containing a p-aminophenol derivative of formula (I) as developer give hair colorations of excellent color stability, particularly in terms of light fastness, wash fastness and rubbing fastness. As far as the dyeing properties are concerned, the hair colorants of the invention provide a wide range of different color shades from blond to brown to purple, violet and even blue and black, depending on the kind and composition of the dye components used. The shades stand out by their unusual color intensity and good color balancing between damaged and un-damaged hair. The very good coloring properties of the hair colorants of the present patent application also manifest themselves in that these colorants make it possible to dye gray hair, previously not damaged chemically, without any problems and with good covering power.

The following examples illustrate the object of the invention in greater detail without limiting its scope.

EXAMPLES

Example 1

Synthesis of (p-Aminohydroxyphenyl)acrylamide Derivatives of Formula (I) (General Method of Synthesis)

A. Synthesis of tert.butyl N-(3-bromo-4-hydroxyphenyl)carbamate

A solution of 9.4 g (52.8 mmol) of N-bromosuccinimide in 450 mL of chloroform was added dropwise at 0° C. over a period of 2 hours to a suspension of 10 g (47.8 mmol) of tert.butyl N-(4-hydroxyphenyl)carbamate in 100 mL of chloroform. The reaction mixture was allowed to agitate for an additional 15 min after which it was washed twice with water (first with 400 ml, then with 200 mL), dried with magnesium sulfate and filtered, and the filtrate was partly evaporated. Hexane was then added to the residue with agitation, which caused a precipitate to form. The precipitate was filtered off and washed with hexane.

This gave 9.7 g (70% of the theoretical) of tert.butyl N-(3-bromo-4-hydroxyphenyl)carbamate.

B. Synthesis of tert.butyl N-(3-bromo-4-ethoxymethoxyphenyl)carbamate 0.76 g (17.4 mmol) of a sodium hydride dispersion (55% in oil) was added portionwise at 0° C. to a solution of 5 g (17.4 mmol) of tert.butyl N-(3-bromo-4-hydroxyphenyl)carbamate in 60 mL of tetrahydrofuran. The mixture was allowed to agitate 50 min at 0° C. after which 1.83 g (19.4 mmol) of chloromethyl ethyl ether was added. The mixture was allowed to agitate at 0° C. for an additional hour. It was then poured onto ice and extracted with ethyl acetate, and the organic phase was washed with a saturated aqueous sodium chloride solution, dried over $Na_2SO_4$ and filtered, and the filtrate was evaporated. The residue was purified on silica gel with petroleum ether/ethyl acetate (9:1).

This gave 4.8 g (80% of the theoretical) of tert.butyl N-(3-bromo-4-ethoxymethoxyphenyl)carbamate.
$^1$H-NMR (300 MHz, $CDCl_3$): δ=7.67 (d, 1H); 7.16 (dd, 1H); 7.07 (d, 1H); 5.23 (s, 2H); 3.77 (q, 2H); 1.51 (s, 9H); 1.22 (t, 3H).

C. Synthesis of tert.butyl N-(4-ethoxymethoxy-3-formylphenyl)carbamate 3.3 g (0.01 mol) of tert.butyl (3-bromo-4-ethoxymethoxyphenyl)-carbamate from step B was dissolved under argon in 100 mL of anhydrous tetrahydrofuran. Then, 17 mL (=0.03 mol) of a 1.6-molar solution of methyllithium in ether was added stepwise. The reaction mixture was then cooled to −20° C., and to it was added stepwise 7 mL (=0.01 mol) of a 1.5-molar solution of tert.butyl-lithium. At the end of the addition, the solution was allowed to agitate for an additional 30 min at the indicated temperature. Then, 1.2 g (0.02 mol) of dimethylformamide was added, and the reaction mixture was allowed to agitate at −20° C. for 1 hour. It was then heated slowly to 0° C. and hydrolyzed with a 10% phosphate buffer solution and poured onto ethyl acetate. The aqueous phase was extracted with ethyl acetate, and the organic phase was dried with magnesium sulfate. The solvent was distilled off in a rotary evaporator, and hexane was added to the residue. The resulting yellow precipitate was then filtered off, washed with hexane and dried.

This gave 2.0 g (70% of the theoretical) of tert.butyl N-(4-ethoxymethoxy-3-formylphenyl)carbamate.
$^1$H-NMR (300 MHz, $CDCl_3$): δ=10.43 (s, 1H); 7.73 (d 1H); 7.61 (d, 1H); 7.20 (d, 1H); 6.45 (br, 1H); 5.31 (s, 2H); 3.75 (q, 2H); 1.51 (s, 9H); 1.23 (t, 3H).

D. Synthesis of methyl 3-(5-tert.butoxycarbonylamino-2-ethoxymethoxyphenyl)acrylate 8.9 g (0.03 mol) of tert.butyl N-(ethoxymethoxy-2-formylphenyl)carbamate from step C was dissolved in 70 mL of tetrahydrofuran and to the resulting solution was added 11.9 g (0.036 mol) of methoxycarbonylmethylene triphenylphosphorane. The reaction mixture was allowed to agitate 3 hours at room temperature. The mixture was then poured into water and extracted with ethyl acetate, and the organic phase was washed with saturated aqueous sodium chloride solution, dried over sodium sulfate and filtered, and the filtrate was evaporated.

Flash chromatography of the crude product on silica gel with hexane/ethyl acetate gave 10.5 g (95% of the theoretical) of product. The product was suspended in hexane/diethyl ether (10:1), and the pure E-isomer was obtained by crystallization from ethyl acetate/hexane.
$^1$H-NMR (300 MHz, $CDCl_3$): δ=7.99 (d, 1H); 7.60 (br s, 1H); 7.26 (dd, 1H); 7.12 (d, 1H); 6.50 (d, 1H); 6.42 (br s, 1H); 5.25 (s, 2H); 3.79 (s, 3H); 3.73 (q, 2H); 1.51 (s, 9H); 1.21 (t, 3H).

E. Synthesis of 3-(5-tert.butoxycarbonylamino-2-ethoxymethoxyphenyl)acrylic acid 2.53 g (0.06 mol) of lithium hydroxide monohydrate was added at 0° C. to a solution of 6.3 g (0.018 mol) of methyl 3-(5-tert.butoxycarbonylamino-2-ethoxymethoxyphenyl) acrylate from step D in 50 mL of tetrahydrofuran, 15 mL of methanol and 30 mL of water. The mixture was allowed to agitate 24 hours at 60° C. The reaction mixture was then poured onto a phosphate buffer solution (pH 7.0) and extracted with ethyl acetate, and the organic phase was washed with a saturated aqueous sodium chloride solution and then dried over sodium sulfate. The organic phase was partially evaporated to incipient formation of a precipitate, and hexane was then added. The precipitate was filtered off and washed with 50 mL of hexane. This gave 5.4 g (89% of the theoretical) of 3-(5-tert.butoxycarbonylamino-2-ethoxymethoxyphenyl)acrylic acid.

¹H-NMR (300 MHz, DMSO-D₆): δ=12.4 (br, 1H); 9.22 (br s, 1H); 7.81 (d, 1H); 7.73 (d, 1H); 7.42 (dd, 1H); 7.10 (d, 1H); 6.33 (d, 1H); 5.27 (s, 2H); 3.67 (q, 2H); 1.48 (s, 9H); 1.13 (t, 3H).

F. Synthesis of 3-(5-amino-2-hydroxyphenyl)acrylamide derivatives

A mixture of 0.07 g (0.185 mmol) of 3-(5-tert.butoxycarbonylamino-2-ethoxymethoxyphenyl)acrylic acid, 0.037 g (0.24 mmol) of N-hydroxybenzotriazole hydrate and 0.043 g (0.22 mmol) of N-(3-dimethylaminopropyl-N'-ethylcarbodiimide hydrochloride in dichloromethane was charged to a reactor. To it were added the appropriate amine (0.22 mol) and 0.047 g of N-ethyldiisopropylamine, and the mixture was allowed to shake for 12 hours at room temperature. At the end of the reaction, the reaction mixture was poured into 10 mL of ethyl acetate. The organic phase was then ex-tracted with sodium hydrogen carbonate and dried with magnesium sulfate. The sol-vent was distilled off in a rotary evaporator and the residue was purified on silica gel with an appropriate eluent (for example, petroleum ether/ethyl acetate or dichloro-methane/methanol). The resulting product in 4 mL of ethanol was heated to 50° C. To prepare the hydrochloride, 1.5 mL of a 2.9-molar ethanolic hydrochloric acid solution was added dropwise. The solution was evaporated, and the residue was dried.

a. 3-(5-Amino-2-hydroxyphenyl)-N-ethylacrylamide hydrochloride
  Amine used: ethylamine
  Mass spectrum: MH⁺ 207 (100)
b. 3-(5-Amino-2-hydroxyphenyl)-N-(4-aminophenyl)acrylamide hydrochloride
  Amine used: 4-hydroxy-1-aminobenzene
  Mass spectrum: MH⁺ 271 (100)
c. 3-(5-Amino-2-hydroxyphenyl)-N-(4-aminophenyl)acrylamide hydrochloride
  Amine used: tert.butyl 4-aminophenylcarbamate
  Mass spectrum: MH⁺ 270 (100)
d. N-[4-Amino-2-(2-hydroxyethyl)-2H-pyrazol-3-yl]-3-(5-amino-2-hydroxyphenylyacrylamide hydrochloride
  Amine used: 4,5-diamino-1-(2-hydroxyethyl)pyrazole
  Mass spectrum: MH⁺ 269 (100)
e. N-Allyl-3-(5-amino-2-hydroxyhenyl)acrylamide hydrochloride
  Amine used: allylamine
  Mass spectrum: MH⁺ 304 (100)
f. 3-(5-Amino-2-hydroxyphenyl)-N-cylopropylacrylamide hydrochloride
  Amine used: cyclopropylamine
  Mass spectrum: MH⁺ 219 (100)
g. N-(2-Aminoethyl)-3-(5-amino-2-hydroxyphenyl)acrylamide hydrochloride
  Amine used: ethylenediamine
  Mass spectrum: MH⁺ 222 (100)
h. 3-(5-Amino-2-hydroxyphenyl)-N-[4-amino-2(3)-methylphenyl]acrylamide hydrochloride
  Amine used: tert.butyl (4-amino-2-methylphenyl) carbamate and tert.butyl (4-amino-3-methylphenyl) carbamate
  Mass spectrum: MH⁺ 284 (100)
i. 3-(5-Amino-2-hydroxyphenyl)-N-isopropylacrylamide hydrochloride
  Amine used: isopropylamine
  Mass spectrum: MH⁺ 221 (100)
j. 3-(5-Amino-2-hydroxyphenyl)-N-propylacrylamide hydrochloride
  Amine used: propylamine
  Mass spectrum: MH⁺ 221 (100)
k. 3-(5-Amino-2-hydroxyphenyl)-1-pyrrolidin-1-ylpropenone hydrochloride
  Amine used: pyrrolidine
  Mass spectrum: MH⁺ 233 (100)
l. 3-(5-Amino-2-hydroxyphenyl)-N-(2-methoxyethyl) acrylamide hydrochloride
  Amine used: 2-methoxyethylamine
  Mass spectrum: MH⁺ 237 (100)
m. 3-(5-Amino-2-hydroxyphenyl)-1-morpholin-4-ylpropenone hydrochloride
  Amine used: morpholine
  Mass spectrum: MH⁺ 249 (100)
n. 3-(5-Amino-2-hydroxyphenyl)-N-(1-hydroxymethylpropyl)acrylamide hydrochloride
  Amine used: 2-amino-1-butanol
  Mass spectrum: MH⁺ 251 (100)
o. 3-(5-Amino-2-hydroxyphenyl)-N-furan-2-ylmethylacrylamide hydrochloride
  Amine used: furfurylamine
  Mass spectrum: MH⁺ 259 (100)
p. 3-(5-Amino-2-hydroxyphenyl)-N-methoxy-N-methylacrylamide hydrochloride
  Amine used: N,O-dimethylhydroxylamine hydrochloride
  Mass spectrum: MH⁺ 223 (100)
q. 3-(5-Amino-2-hydroxyphenyl)-1-(4-methylpiperazin-1-yl)propenone hydrochloride
  Amine used: 4-methylpiperazine
  Mass spectrum: MH⁺ 262 (100)
r. 3-(5-Amino-2-hydroxyphenyl)-1-(4-hydroxypiperidin-1-yl)propenone hydrochloride
  Amine used: 4-hydroxypiperidine
  Mass spectrum: MH⁺ 263 (100)
s. N-(2-Acetylaminoethyl)-3-(5-amino-2-hydroxyphenyl)acrylamide hydrochloride
  Amine used: N-acetylethylenediamine
  Mass spectrum: MH⁺ 264 (100)
t. 3-(5-Amino-2-hydroxyphenyl)-N-(2-morpholin-4-ylethyl)acrylamide hydrochloride
  Amine used: 4-(2-ethylamino)morpholine
  Mass spectrum: MH⁺ 292 (100)
u. 3-(5-Amino-2-hydroxyphenyl)-N-[3-(2-ketopyrrolidin-1-yl)propyl]acrylamide hydrochloride
  Amine used: 1-(3-aminopropyl)-2-pyrrolidone
  Mass spectrum: MH⁺ 304 (100)
v. 3-(5-Amino-2-hydroxyphenyl)-N-(2-hydroxy-1-methylethyl)acrylamide hydrochloride
  Amine used: 2-aminopropanol
  Mass spectrum: MH⁺ 237 (100)
w. 3-(5-Amino-2-hydroxyphenyl)-N-[2-(5-nitropyridin-2-ylamino)ethyl]acrylamide hydrochloride
  Amine used: 2-amino-5-nitropyridine
  Mass spectrum: MH⁺ 344 (100)
x. 3-(5-Amino-2-hydroxyphenyl)-N-(3-imidazol-1-ylpropyl)acrylamide hydrochloride
  Amine used: 1-(3-aminopropyl)imidazole
  Mass spectrum: MH⁺ 287 (100)
y. 3-(5-Amino-2-hydroxyphenyl)-N-(tetrahydrofuran-2-ylmethyl)acrylamide hydrochloride
  Amine used: tetrahydrofurfurylamine
  Mass spectrum: MH⁺ 263 (100)
z. N-[4-Amino-2(3)-(2-hydroxyethyl)phenyl]-3-(5-amino-2-hydroxyphenyl)acrylamide hydrochloride
  Amine used: tert.butyl [4-amino-2-(2-hydroxyethyl) phenyl]carbamate and tert.butyl [4-amino-3-(2-hydroxyethyl)phenyl]carbamate Mass spectrum: MH⁺ 314 (100)
aa. 3-(5-Amino-2-hydroxyphenyl)-N-{4-[bis-(2-hydroxyethyl)amino]phenyl}acrylamide hydrochloride
   Amine used: 4-bis-(2-hydroxyethyl)aminoaniline
   Mass spectrum: MH⁺ 358 (100)
ab. 3-(5-Amino-2-hydroxyphenyl)-N-(3-aminophenyl)acrylamide hydrochloride
   Amine used: tert.butyl (3-aminophenyl)carbamate
   Mass spectrum: MH⁺ 270 (100)
ac. N-[5-Amino-2(4)-(2-hydroxyethoxy)phenyl]-3-(5-amino-2-hydroxyphenyl)acrylamide hydrochloride
   Amine used: tert.butyl [3-amino-4-(2-hydroxyethoxy)phenyl]carbamate and tert.butyl [3-amino-6-(2-hydroxyethoxy)phenyl]carbamate
   Mass spectrum: MH⁺ 330 (100)
ad. 3-(5-Amino-2-hydroxyphenyl)-N-[2-chloro-4-(2-hydroxyethylamino)-5-nitrophenyl]acrylamide hydrochloride
   Amine used: 2-chloro-4-(2-hydroxyethyl)amino-5-nitroaniline
   Mass spectrum: MH⁺ 393 (100)
ae. 3-(5-Amino-2-hydroxyphenyl)-N-benzo[1,3]dioxol-5-ylacrylamide hydrochloride
   Amine used: benzo[1,3]dioxol-5-ylamine
   Mass spectrum: MH⁺ 299 (100)
af. 3-(5-Amino-2-hydroxyphenyl)-N-(2-hydroxyethyl)-N-methylacrylamide hydrochloride
   Amine used: 2-methylaminoethanol
   Mass spectrum: MH⁺ 237 (100)
ag. 3-(5-Amino-2-hydroxyphenyl)-N-ethyl-N-(2-hydroxyethyl)acrylamide hydrochloride
   Amine used: 2-ethylaminoethanol
   Mass spectrum: MH⁺ 251 (80)
ah. 3-(5-Amino-2-hydroxyphenyl)-1-(2-hydroxymethylpyrrolidin-1-yl)propenone hydrochloride
   Amine used: prolinol
   Mass spectrum: MH⁺ 263 (100)
ai. 1-[3-(5-Amino-2-hydroxyphenyl)acryloyl]pyrrolidine-2-carboxamide hydrochloride
   Amine used: prolinamide
   Mass spectrum: MH⁺ 276 (100)
aj. 3-(5-Amino-2-hydroxyphenyl)-1-(3-hydroxypiperidin-1yl)propenone hydrochloride
   Amine used: 3-hydroxypiperidine
   Mass spectrum: MH⁺ 263 (100)
ak. 3-(5-Amino-2-hydroxyphenyl)-N-(2-hydroxy-1-hydroxymethylethyl)acrylamide hydrochloride
   Amine used: 3-amino-1,2-propanediol
   Mass spectrum: MH⁺ 253 (100)
al. 2-[3-(5-Amino-2-hydroxyphenyl)acryloylamino]-3-methylbutyric acid hydrochloride
   Amine used: α-aminoisovaleric acid
   Mass spectrum: MH⁺ 279 (100)
am. 3-(5-Amino-2-hydroxyphenyl)-N-(1-carbamoyl-2-hydroxyethyl)acrylamide hydrochloride
   Amine used: 2-amino-3-hydroxypropionamide
   Mass spectrum: MH⁺ 266 (100)
an. 3-(5-Amino-2-hydroxyphenyl)-N-(3-hydroxy-4-methylphenyl)acrylamide hydrochloride
   Amine used: 5-amino-2-methylphenol
   Mass spectrum: MH⁺ 285 (100)
ao. 3-(5-Amino-2-hydroxyphenyl)-N-(2-hydroxy-5-nitrophenyl)acrylamide hydrochloride
   Amine used: 2-amino-4-nitrophenol
   Mass spectrum: MH⁺ 316 (100)

Examples 2 to 39

Hair Colorants

Hair colorant solutions having the following composition were prepared:

| 1.25 mmol | of developer of formula (I) as per Table 1 |
| 1.25 mmol | of coupler according to Table 1 |
| 1.0 g | of potassium oleate (8% aqueous solution) |
| 1.0 g | of ammonia (22% aqueous solution) |
| 1.0 g | of ethanol |
| 0.3 g | of ascorbic acid |
| to 100.0 g | water |

Just before use, 30 g of the foregoing coloring solution was mixed with 30 g of a 6% aqueous hydrogen peroxide solution. The mixture was then applied to bleached hair. After an exposure time of 30 min at 40° C., the hair was rinsed with water, washed with a commercial shampoo and dried. The resulting color shades are presented in Table 1.

TABLE 1

| Example No. | Developer of formula (I) | Coupler II. 1,3-Diamino-4-(2-hydroxy-ethoxy)benzene sulfate | III. 5-Amino-2-methyl-phenol | IV 1-Naphthol |
| --- | --- | --- | --- | --- |
| 2 | As per Ex. 1a | red-brown | red-orange | violet |
| 3 | As per Ex. 1b | red-brown | red-orange | violet |
| 4 | As per Ex. 1c | red-brown | red-orange | violet |
| 5 | As per Ex. 1d | red-brown | red-orange | bright violet |
| 6 | As per Ex. 1e | red-brown | red-orange | bright violet |
| 7 | As per Ex. 1f | red-brown | red-orange | bright violet |
| 8 | As per Ex. 1g | red-brown | red-orange | bright violet |
| 9 | As per Ex. 1h | red-brown | red-orange | bright violet |
| 10 | As per Ex. 1i | red-brown | red-orange | bright violet |
| 11 | As per Ex. 1j | red-brown | red-orange | bright violet |
| 12 | As per Ex. 1k | red-brown | red-orange | bright violet |
| 13 | As per Ex. 1l | red-brown | red-orange | bright violet |
| 14 | As per Ex. 1m | red-brown | red-orange | bright violet |
| 15 | As per Ex. 1n | red-brown | red-orange | bright violet |
| 16 | As per Ex. 1o | red-brown | red-orange | bright violet |
| 17 | As per Ex. 1p | red-brown | red-orange | bright violet |
| 18 | As per Ex. 1q | red-brown | red-orange | bright violet |
| 19 | As per Ex. 1r | red-brown | brown | bright violet |
| 20 | As per Ex. 1s | red-brown | red-brown | bright violet |
| 21 | As per Ex. 1t | red-brown | red-orange | bright violet |
| 22 | As per Ex. 1u | red-brown | red-orange | bright violet |
| 23 | As per Ex. 1v | red-brown | red-orange | bright violet |
| 24 | As per Ex. 1x | red-brown | bright red-orange | bright violet |
| 25 | As per Ex. 1y | red-brown | bright red-orange | bright violet |
| 26 | As per Ex. 1z | red-brown | bright red-orange | bright violet |
| 27 | As per Ex. 1aa | red-brown | red | bright violet |
| 28 | As per Ex. 1ab | red-brown | bright red-orange | bright violet |
| 29 | As per Ex. 1ac | red-brown | bright red-orange | bright violet |
| 30 | As per Ex. 1ae | red-brown | bright red-orange | bright violet |
| 31 | As per Ex. 1af | red-brown | bright red-orange | bright violet |
| 32 | As per Ex. 1ag | red-brown | bright red-orange | bright violet |
| 33 | As per Ex. 1ah | red-brown | bright red-orange | bright violet |
| 34 | As per Ex. 1ai | red-brown | bright red-orange | bright violet |
| 35 | As per Ex. 1aj | red-brown | bright red-orange | bright violet |
| 36 | As per Ex. 1ak | red-brown | bright red-orange | bright violet |
| 37 | As per Ex. 1al | red-brown | bright red-orange | bright violet |
| 38 | As per Ex. 1m | red-brown | bright red-orange | bright violet |

TABLE 1-continued

| Example No. | Developer of formula (I) | Coupler II. 1,3-Diamino-4-(2-hydroxy-ethoxy)benzene sulfate | III. 5-Amino-2-methyl-phenol | IV 1-Naphthol |
|---|---|---|---|---|
| 39 | As per Ex. 1n | red-brown | bright red-orange | bright violet |

Examples 40 to 71

Hair Colorants

Hair colorant solutions of the following composition were prepared:

| | |
|---|---|
| X g | of developer E1 or E2 of formula (I), as per Table 3 |
| U g | of developer E3 to E10 as per Table 3 |
| Y g | of coupler K11 to K36 as per Table 4 |
| Z g | of direct dye D1 to D3 as per Table 2 |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Just before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. Table 5 shows the coloring results.

Examples 72 to 77

Hair Colorants

Dye carriers in cream form and having the following composition were prepared:

| | |
|---|---|
| X g | of developer E1 of formula (I) as per Table 3 |
| U g | of developer E3 to E10 as per Table 3 |
| Y g | of coupler K11 to K36 as per Table 4 |
| Z g | of direct dye D1 to D3 as per Table 2 |
| 15.0 g | of cetyl alcohol |
| 0.3 g | of ascorbic acid |
| 3.5 g | of sodium lauryl alcohol diethylene glycol ether sulfate, 28% aqueous solution |
| 3.0 g | of ammonia, 22% aqueous solution |
| 0.3 g | of sodium sulfite, anhydrous |
| to 100 g | water |

Just before use, 30 g of the foregoing coloring cream was mixed with 30 g of a 6% solution of hydrogen peroxide. The mixture was then applied to the hair. After an exposure time of 30 min, the hair was rinsed with water, washed with a commercial shampoo and dried. The coloring results are presented in Table 6 hereinbelow.

TABLE 2

| | Direct Dyes |
|---|---|
| D1 | 2,6-diamino-3-[(pyridin-3-yl)azo]pyridine |
| D2 | 6-chloro-2-ethylamino-4-nitrophenol |
| D3 | 2-amino-6-chloro-4-nitrophenol |

TABLE 3

| | Developers |
|---|---|
| E1 | 3-(5-amino-2-hydroxyphenyl)-N-ethyl-acrylamide hydrochloride |
| E2 | 3-(5-amino-2-hydroxyphenyl)-N-(4-aminophenyl)-acrylamide hydrochloride |
| E3 | 2,5-diaminophenylethanol sulfate |
| E4 | 3-methyl-4-aminophenol |
| E5 | 4-amino-2-aminomethylphenol dihydrochloride |
| E6 | 4-aminophenol |
| E7 | N,N-bis-(2'-hydroxyethyl)-p-phenylenediamine sulfate |
| E8 | 4,5-diamino-1-(2'-hydroxyethyl)pyrazole sulfate |
| E9 | 2,5-diaminotoluene sulfate |
| E10 | 1,4-diaminobenzene |

TABLE 4

| | Couplers |
|---|---|
| K11 | 1,3-diaminobenzene |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K16 | 3,5-diamino-2,6-dimethoxypyridine dihydrochloride |
| K17 | 2,4-diamino-5-ethoxytoluene sulfate |
| K18 | N-(3-dimethylamino)phenylurea |
| K19 | 1,3-bis-(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K26 | 1-acetoxy-2-methylnaphthalene |
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylenedioxy-benzene hydrochloride |
| K35 | 3,4-methylenedioxyphenol |
| K36 | 2-amino-5-methylphenol |

TABLE 5

| | Hair Colorants | | | | | |
|---|---|---|---|---|---|---|
| Example | 40 | 41 | 42 | 43 | 44 | 45 |
| Dyes | (Quantity of dyes in grams) | | | | | |
| E1 | 0.096 | 0.24 | 0.30 | 0.04 | 0.01 | 0.70 |
| E9 | | | | | 0.096 | 1.80 |
| E10 | | | 0.90 | | | |
| K11 | | | | | | 0.05 |
| K12 | | | | | 0.01 | |
| K18 | | | | | | 0.03 |
| K21 | | | | | 0.02 | 0.06 |
| K22 | 0.08 | 0.20 | 0.25 | 0.056 | | 0.42 |
| K24 | | | | 0.05 | | 0.11 |
| K25 | | | | | 0.03 | |
| K31 | | | | 0.20 | | 0.80 |
| K32 | | 0.03 | 0.05 | 0.316 | | |
| K35 | 0.018 | | | | | |
| K36 | | 0.03 | 0.05 | 0.01 | | |
| K26 | | | | | | |

TABLE 5-continued

Hair Colorants

| Dyes | | | | | | |
|---|---|---|---|---|---|---|
| D1 | | | | 0.01 | | |
| D3 | 0.04 | 0.06 | 0.025 | | | |
| Color shade | bright-blond to copper-gold | copper-gold | bright copper color | purple-brown | silver-blond | dark mahogany |

| Example | 46 | 47 | 48 | 49 | 50 | 51 |
|---|---|---|---|---|---|---|
| Dyes | (Quantity of dyes in grams) | | | | | |
| E1 | 0.01 | 0.60 | 1.00 | 0.20 | 0.80 | 0.60 |
| E10 | 2.00 | | | 1.90 | | |
| E3 | | 0.05 | | | | |
| E7 | | | 0.06 | | | |
| E8 | | | 1.00 | | | |
| E9 | | | | | 1.00 | 0.70 |
| K12 | | | 1.10 | | | |
| K13 | 0.07 | | | | | 0.80 |
| K16 | | | | | | 1.00 |
| K17 | | | 1.10 | | | |
| K18 | | | | 1.25 | | |
| K21 | 0.40 | | | 0.28 | | |
| K22 | 0.08 | 0.40 | | | | |
| K24 | | 0.10 | | | | |
| K25 | | | | | 0.80 | |
| K31 | 0.80 | | | | | |
| K32 | | 0.03 | | | | |
| K33 | | | | | 0.75 | |
| K36 | | 0.03 | | | | |
| D1 | | 0.25 | | | | |
| D3 | | 0.15 | | | | |
| Color shade | black-brown | orange | blue-violet | blue-red | pink colors | Bordeaux colors |

| Example | 52 | 53 | 54 | 55 | | |
|---|---|---|---|---|---|---|
| Dyes | (Quantity of dyes in grams) | | | | | |
| E1 | 0.01 | 0.01 | 0.05 | 0.60 | | |
| E3 | 1.40 | 4.50 | | | | |
| E5 | | | | 0.25 | | |
| E6 | | | 0.10 | | | |
| E8 | | 0.80 | 0.50 | 0.01 | | |
| E9 | 2.50 | | | | | |
| K12 | 0.60 | | | | | |
| K13 | 0.20 | | | 0.80 | | |
| K14 | | 0.25 | | | | |
| K16 | 0.01 | | | | | |
| K18 | | | | 1.25 | | |
| K19 | 0.80 | | | | | |
| K21 | 0.30 | | | 0.28 | | |
| K22 | | 5.00 | | | | |
| K25 | | 0.40 | | | | |
| K23 | | | 0.60 | | | |
| K31 | 1.10 | | | | | |
| K32 | | | | 0.33 | | |
| K36 | | | 0.19 | | | |
| D2 | | | 0.50 | | | |
| Shade | black | red-violet | red-orange | warm yellow | | |

| Example | 56 | 57 | 58 | 59 | 60 | 61 |
|---|---|---|---|---|---|---|
| Dyes | (Quantity of dyes in grams) | | | | | |
| E2 | 0.096 | 0.24 | 0.30 | 0.04 | 0.01 | 0.70 |
| E10 | | | | 0.90 | | |
| E9 | | | | | 0.096 | 1.80 |
| K12 | | | | 0.01 | | |
| K18 | | | | | | 0.03 |
| K21 | | | | | 0.02 | 0.06 |
| K22 | 0.08 | 0.20 | 0.25 | 0.056 | | 0.58 |
| K25 | | | | | 0.03 | |
| K31 | | | | 0.20 | | 0.80 |
| K32 | | 0.03 | 0.05 | 0.316 | | |
| K35 | 0.018 | | | | | |
| K36 | | | 0.03 | 0.05 | 0.01 | |

TABLE 5-continued

Hair Colorants

| Dyes | | | | | | |
|---|---|---|---|---|---|---|
| K26 | | | | | | |
| D1 | | | | 0.01 | | |
| D3 | 0.04 | 0.06 | 0.025 | | | |
| Color shade | bright-blond to copper-gold | copper-gold | bright copper colors | purple-brown | silver-blond | dark mahogany |

| Example | 62 | 63 | 64 | 65 | 66 | 67 |
|---|---|---|---|---|---|---|
| Dyes | (Quantity of dyes in grams) | | | | | |
| E2 | 0.01 | 0.60 | 1.00 | 0.20 | 0.80 | 0.60 |
| E10 | 2.00 | | | 1.90 | | |
| E3 | | 0.05 | | | | |
| E8 | | | 1.00 | | | |
| E9 | | | | | 1.00 | 0.70 |
| K12 | | | 1.10 | | | |
| K13 | 0.07 | | | | | 0.80 |
| K16 | | | | | | 1.00 |
| K17 | | | 1.10 | | | |
| K18 | | | | 1.25 | | |
| K21 | 0.40 | | | 0.28 | | |
| K22 | 0.08 | 0.50 | | | | |
| K25 | | | | | 0.80 | |
| K31 | 0.80 | | | | | |
| K32 | | 0.03 | | | | |
| K33 | | | | | 0.75 | |
| K36 | | 0.03 | | | | |
| D1 | | 0.25 | | | | |
| D3 | | 0.15 | | | | |
| Color shade | black-brown | orange | blue-violet | blue-red | pink colors | Bordeaux colors |

| Example | 68 | 69 | 70 | 71 | |
|---|---|---|---|---|---|
| Dyes | (Quantity of dyes in grams) | | | | |
| E2 | 0.01 | 0.01 | 0.05 | 0.60 | |
| E3 | 1.40 | 4.50 | | | |
| E5 | | | | 0.25 | |
| E6 | | | 0.10 | | |
| E8 | | 0.80 | 0.50 | 0.01 | |
| E9 | 2.70 | | | | |
| K12 | 0.60 | | | | |
| K13 | 0.20 | | | 0.80 | |
| K14 | | 0.25 | | | |
| K16 | 0.01 | | | | |
| K18 | | | | 1.25 | |
| K19 | 0.80 | | | | |
| K21 | 0.30 | | | 0.28 | |
| K22 | | 5.00 | | | |
| K25 | | 0.40 | | | |
| K23 | | | 0.60 | | |
| K31 | 1.10 | | | | |
| K32 | | | | 0.33 | |
| K34 | 0.20 | | | | |
| K36 | | | 0.19 | | |
| D2 | | | 0.50 | | |
| Shade | black | red-violet | red-orange | warm yellow | |

TABLE 6

Hair Colorants

| | Example | | | | | |
|---|---|---|---|---|---|---|
| Dyes | 72 | 73 | 74 | 75 | 76 | 77 |
| | (Quantity of dyes in grams) | | | | | |
| E1 | 0.10 | 0.20 | 0.01 | 2.00 | 0.50 | 0.70 |
| E4 | | | | | | 1.60 |
| E8 | | | | 0.25 | 0.80 | 0.20 |
| E9 | 3.20 | 1.71 | 0.02 | | | 1.80 |

TABLE 6-continued

Hair Colorants

| Dyes | Example |  |  |  |  |
|---|---|---|---|---|---|
|  | 72 | 73 | 74 | 75 | 76 | 77 |
|  | (Quantity of dyes in grams) |  |  |  |  |  |
| K13 | 0.23 | 0.10 |  |  | 1.30 |  |
| K14 | 0.20 |  |  |  |  |  |
| K16 |  |  | 0.015 |  |  |  |
| K21 | 0.40 | 0.80 |  |  | 0.02 |  |
| K22 | 0.08 |  | 0.25 | 1.80 |  | 4.50 |
| K23 |  | 0.20 |  |  | 0.03 |  |
| K31 | 1.05 | 0.135 | 0.02 | 0.25 |  | 0.80 |
| K25 |  |  |  |  |  | 0.55 |
| K26 |  |  | 0.03 |  |  |  |
| K19 |  |  |  |  | 1.70 |  |
| K36 |  | 0.27 |  |  |  |  |
| D2 |  | 0.01 |  |  |  |  |
| Color shade | dark brown | choco- late brown | silver blond | orange colors | blue- violet | red- violet |

Unless otherwise indicated, all percentages in the present patent application are by weight.

What is claimed is:

1. A (p-aminohydroxyphenyl)acrylamide derivative of formula (I), or a physiologically tolerated, water-soluble salt thereof:

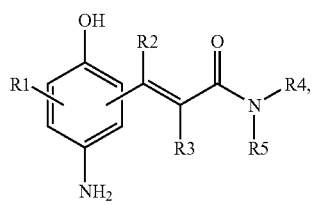

(I)

wherein
R1 denotes hydrogen, a halogen atom, a $C_1$–$C_4$-alkyl group, a $C_1$–$C_4$-hydroxyalkyl group or a $C_1$–$C_4$-alkoxy group;
R2 and R3 independently of each other denote hydrogen or a $C_1$–$C_6$-alkyl group;
R4 denotes a $C_1$–$C_2$-alkyl group, a methoxy group or a $C_2$–$C_4$-hydroxyalkyl group;
R5 denotes a $C_2$–$C_4$-hydroxyalkyl group;
R6 denotes hydrogen, a carboxy group or an aminocarbonyl group;
R7 and R8, independently of each other, denote hydrogen, a hydroxyl group, an aminocarbonyl group, a methylthiomethyl group, a phenyl-substituted or hydroxyl-substituted phenyl group or a group of formula

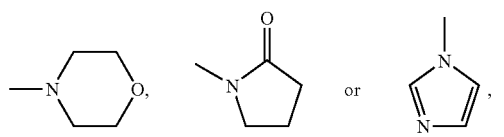

R9, R10, R11, R12 and R13, independently of each other, denote hydrogen, a halogen atom, a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group, an alkylamino group, a $C_1$–$C_4$-hydroxyalkylamino group, a dialkylamino group, a di($C_1$–$C_4$-hydroxyalkyl)amino group, a ($C_3$–$C_4$-dihydroxyalkyl)-amino group, a ($C_1$–$C_4$-hydroxyalkyl)-$C_1$–$C_4$-alkylamino group, a trifluoromethyl group, a —C(O)H group, a —C(O)CH$_3$— group, a —C(O)CF$_3$ group, an —Si(CH$_3$)$_3$ group, a $C_1$–$C_4$-hydroxyalkyl group or a $C_3$–$C_4$-dihydroxyalkyl group, or two adjacent R9 to R13 groups form an —O—CH$_2$—O— bridge;

R14 denotes a $C_1$–$C_4$-alkyl group, a benzyl group or a $C_2$–$C_4$-hydroxyalkyl group;

R15 denotes hydrogen or a $C_1$–$C_6$-alkyl group;

R16 denotes hydrogen, a hydroxyl group, a carboxy group, an aminocarbonyl group or a hydroxymethyl group; and R17 denotes hydrogen or a $C_1$–$C_6$-alkyl group.

2. A (p-aminohydroxyphenyl)acrylamide derivative selected from the group consisting of 3-(5-amino-2-hydroxyphenyl)-N-ethylacrylamide, 3-(2-amino-5-hydroxyphenyl)-N-ethylacrylamide, 3-(5-amino-2-hydroxyphenyl)-N-(4-hydroxyphenyl)acrylamide, 3-(2-amino-5-hydroxyphenyl)-N-(4-hydroxy-phenyl)-acrylamide, 3-(5-amino-2-hydroxyphenyl)-N-(4-aminophenyl)acrylamide, 3-(2-amino-5-hydroxyphenyl)-N-(4-aminophenyl)acrylamide, or a physiologically tolerated salt thereof.

3. An agent for oxidative dyeing of keratin fibers, wherein said agent comprises at least one developer and at least one coupler, said at least one developer comprising at least one (p-aminohydroxyphenyl)acrylamide derivative of formula (I), or a physiologically-tolerated, water-soluble salt thereof:

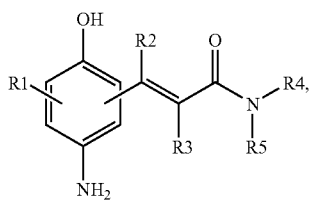

(I)

wherein
R1 denotes hydrogen, a halogen atom, a $C_1$–$C_4$-alkyl group, a $C_1$–$C_4$-hydroxyalkyl group or a $C_1$–$C_4$-alkoxy group;
R2 and R3, independently of each other, denote hydrogen or a $C_1$–$C_6$-alkyl group;
R4 and R5, independently of each other, denote hydrogen, a $C_1$–$C_2$-alkoxy group, a $C_1$–$C_6$-alkyl group, an unsaturated a $C_3$–$C_6$-alkyl group, a $C_2$–$C_4$-hydroxyalkyl group, a $C_3$–$C_4$-dihydroxyalkyl group, a $C_2$–$C_4$-aminoalkyl group, a $C_2$–$C_4$-dimethylaminoalkyl group, a $C_2$–$C_4$-acetylaminoalkyl group, a $C_2$–$C_4$-methoxyalkyl group, a $C_2$–$C_4$-ethoxyalkyl group, a $C_1$–$C_4$-cyanoalkyl group, a $C_1$–$C_4$-carboxyalkyl group, a $C_1$–$C_4$-aminocarbonylalkyl group, a pyridylmethyl group, a furfuryl group, a thienylmethyl group, a hydrogenated furfuryl group, a substituted pyridyl group, a group of formula (II)

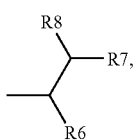

a group of formula (III)

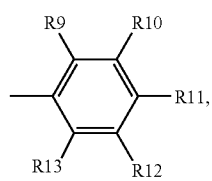

or a group of formula (IV)

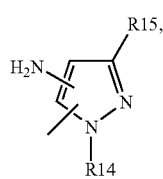

or R4 and R5 together with N form a ring of the following formula:

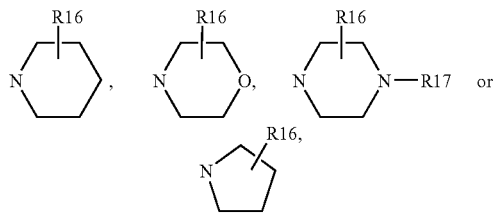

R6 denotes hydrogen, a carboxy group or an aminocarbonyl group;

R7 and R8, independently of each other, denote hydrogen, a hydroxyl group, an aminocarbonyl group, a methylthiomethyl group, a phenyl-substituted or hydroxyl-substituted phenyl group or a group of formula

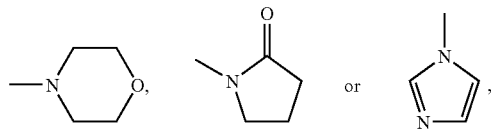

R9, R10, R11, R12 and R13, independently of each other, denote hydrogen, a halogen atom, a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group, an alkylamino group, a $C_1$–$C_4$-hydroxyalkylamino group, a dialkylamino group, a di($C_1$–$C_4$-hydroxyalkyl)amino group, a ($C_3$–$C_4$-dihydroxyalkyl)-amino group, a ($C_1$–$C_4$-hydroxyalkyl)-$C_1$–$C_4$-alkylamino group, a trifluoromethyl group, a —C(O)H group, a —C(O)CH$_3$— group, a —C(O)CF$_3$ group, an —Si(CH$_3$)$_3$ group, a $C_1$–$C_4$-hydroxyalkyl group or a $C_3$–$C_4$-dihydroxyalkyl group, or two adjacent R9 to R13 groups form an —O—CH$_2$—O— bridge;

R14 denotes a $C_1$–$C_4$-alkyl group, a benzyl group or a $C_2$–$C_4$-hydroxyalkyl group;

R15 denotes hydrogen or a $C_1$–$C_6$-alkyl group;

R16 denotes hydrogen, a hydroxyl group, a carboxy group, an aminocarbonyl group or a hydroxymethyl group; and R17 denotes hydrogen or a $C_1$–$C_6$-alkyl group.

4. The agent as defined in claim 3, containing from 0.005 to 20 percent by weight of said at least one (p-aminohydroxyphenyl)acrylamide derivative.

5. The agent as defined in claim 3, wherein the at least one coupler is selected from the group consisting of N-(3-dimethylaminophenyl)urea, 2,6-diamino-pyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 1,3-diamino-4-(3-hydroxypropoxy)benzene, 1,3-diamino-4-(2-methoxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methyl-aminobenzene, 2,4-diaminophenoxyacetic acid, 3-[di(2-hydroxyethyl)amino]-aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino] aniline, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)-amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]-phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methyl-phenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4-(2H)benzoxazine, 6-amino-3,4-dihydro-1,4[2H]benzoxazine, 3-methyl-1- phenyl-5-pyrazolone, 5,6-dihydroxyindole, 5,6-dihydroxyindoline, 5-hydroxyindole, 6-hydroxyindole, 7-hydroxyindole and 2,3-indolinedione.

6. The agent as defined in claim 3, further comprising at least one compound selected from the group consisting of 1,4-diaminobenzene, 1,4-diamino-2-methylbenzene, 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-[2-(acetylamino)ethoxy]-1,4-diaminobenzene, 4-phenyl-aminoaniline, 4-dimethylaminoaniline, 4-diethylaminoaniline, 4-dipropylaminoaniline, 4-[ethyl(2-hydroxyethyl)amino]-aniline, 4-[di(2-hydroxyethyl)amino]aniline, 4-[di(2-hydroxyethyl)amino]-2-methylaniline, 4-[(2-methoxyethyl)-amino]aniline, 4-[(3-hydroxy-propyl)amino]aniline, 4-[(2,3-dihydroxypropyl)-amino]aniline, 1,4-diamino-2-(1-hydroxyethyl)benzene, 1,4-diamino-2-(2-hydroxyethyl)benzene, 1,4-diamino-2-(1-methylethyl)benzene, 1,3-bis-[(4-aminophenyl)(2-hydroxyethyl)amino]-2-propanol, 1,4-bis-[1-(4-aminophenyl)amino]butane, 1,8-bis-(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[2-hydroxyethyl)amino]methylphenol, 4-amino-2-methylphenol, 4-amino-2-(methoxymethyl)-phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol and 1,2,4-trihydroxybenzene.

7. The agent as defined in claim 3, containing from 0.005 to 20 percent by weight of each of said at least one coupler and said at least one developer, based on a total amount of the agent.

8. The agent as defined in claim 3, further comprising at least one direct dye.

9. The agent as defined in claim 3, consisting of a hair colorant.

* * * * *